United States Patent
Lusby et al.

(10) Patent No.: US 12,319,654 B2
(45) Date of Patent: Jun. 3, 2025

(54) INERT NANOCAPSULES (71) Applicant: THE UNIVERSITY COURT OF THE UNIVERSITY OF EDINBURGH, Edinburgh (GB)

(72) Inventors: Paul Lusby, Edinburgh (GB); Michael Burke, Edinburgh (GB); William Grantham, Edinburgh (GB); Steve Archibald, Hull (GB); Benjamin Burke, Hull (GB)

(73) Assignee: THE UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 1084 days.

(21) Appl. No.: 17/260,608

(22) PCT Filed: Jul. 15, 2019

(86) PCT No.: PCT/GB2019/051972
§ 371 (c)(1),
(2) Date: Jan. 15, 2021

(87) PCT Pub. No.: WO2020/016561
PCT Pub. Date: Jan. 23, 2020

(65) Prior Publication Data
US 2022/0177431 A1 Jun. 9, 2022

(30) Foreign Application Priority Data
Jul. 16, 2018 (GB) .................... 1811627

(51) Int. Cl.
*C07D 213/72* (2006.01)
*A61K 51/04* (2006.01)
*C07D 213/22* (2006.01)
*C07D 213/73* (2006.01)

(52) U.S. Cl.
CPC ........ *C07D 213/73* (2013.01); *A61K 51/0474* (2013.01); *C07D 213/22* (2013.01)

(58) Field of Classification Search
None
See application file for complete search history.

(56) References Cited

PUBLICATIONS

Burke et al (Orthogonal Selection and Fixing of Coordination Self-Assembly Pathways for Robust Metallo-organic Ensemble Construction. J. Am. Chem. Soc. 2016, 138, 9308-9315) (Year: 2016).*

Glasson et al (A new Fe(II) quaterpyridyl M4L6 tetrahedron exhibiting selective anion binding. Chem. Commun., 2008, 1190-1192) (Year: 2008).*

Glasson et al., "A new FeII quaterpyridyl M4L6 tetrahedron exhibiting selective anion binding", Chemical Communications, No. 10, p. 1190, XP055628827, ISSN: 1359-7345, DOI: 10.1039/b717740b, UK, Jan. 1, 2008.

Burke et al., "Orthogonal Selection and Fixing of Coordination Self-Assembly Pathways for Robust Metallo-organic Ensemble Construction", Journal of the American Chemical Society, vol. 138, No. 29, pp. 9308-9315, XP055627414, ISSN: 0002-7863, DOI: 10.1021/jacs.6b0534, US, Jun. 28, 2016.

Dionysia Papagiannopoulou, "Technetium-99m radiochemistry for pharmaceutical applications", Journal of Labelled Compounds and Radiopharmaceuticals, vol. 60, No. 11, pp. 502-520, XP055628876, ISSN: 0362-4803, DOI: 10.1002/jlcr.3531, GB, Jun. 15, 2017.

Burke et al., "Visualizing Kinetically Robust ColII4L6 Assemblies in Vivo: SPECT Imaging of the Encapsulated [99mTc]TcO4- Anion", Journal of the American Chemical Society, vol. 140, No. 49, pp. 16877-16881, XP055627412, ISSN: 0002-7863, DOI: 10.1021/jacs.8b09582, US, Nov. 28, 2018.

International Search Report for Application No. PCT/GB2019/051972, mailing date Oct. 11, 2019.

* cited by examiner

Primary Examiner — Jake M Vu
(74) Attorney, Agent, or Firm — MOSER TABOADA (57) ABSTRACT Compounds are presented having the formula $[M_4L_6] \cdot X_n$, where M is a transition metal ion having 6 d-shell valence electrons, X is a counter ion and n is the number of counterions such that the total charge of the compound of formula (I) is zero, and wherein L is a 5-(5-bipyridin-2,2'-yl)-2,2'-bipyridine or derivative thereof. Methods of preparing the compounds and uses of the compounds to retain radiolabels are also presented.

20 Claims, 7 Drawing Sheets

R = H; [Co$^{III}_4$L$^1_6$]12NO$_3$; C-1·12NO$_3$

R = NH$_2$; [Co$^{III}_4$L$^2_6$]12NO$_3$; C-2·12NO$_3$

INERT NANOCAPSULES

FIELD OF THE INVENTION

The invention relates to complexes for the encapsulation of specific species, and methods of delivery of the same, more specifically to complexes to encapsulate radioactive species and methods of delivery of the same.

BACKGROUND

Radioactive isotopes ("radioisotopes") are used in clinical settings for both diagnostic and therapeutic applications. In diagnostic applications, radioisotopes are typically used as labels ("radiolabels") to allow the clinician to see how the blood is flowing in the body or in a specific part of the body, or to label a specific tissue or part of the body, or to locate and understand specific disease states. Such uses are often referred to as "nuclear medicine".

90% of the total usage of medical isotopes is in diagnostic scans. Technetium-99m is the most commonly used isotope in nuclear medicine, accounting for around 80% of the worldwide usage of radioactive isotopes in nuclear medicine. The isotope is attached to molecules which concentrate at the disease site or shows tissue properties within the body. The medical scanning technique is called single-photon emission computed tomography (SPECT) and around 70,000 patients are injected with technetium-99m for diagnostic SPECT scans every day. It is used for blood flow imaging in the heart, detection of whether cancer has spread to bones and to look at blood flow in the brain.

Positron Emission Tomography (PET) is a non-invasive nuclear imaging technique that allows the detection of tracer levels of radiolabelled molecules in vivo. It is the most sensitive molecular imaging technique applied in the clinic, allowing the clinician to obtain functional information on a range of physiological/molecular/biochemical parameters. Currently most of the scans carried out are for the diagnosis and staging of cancer using radiolabelled glucose [$^{18}$F]FDG, to allow for improved patient management as well as the potential for more effective radiotherapy planning. There are also a range of existing and potential applications in cardiology and neuroscience.

A problem of such applications is the need to develop individually-tailored synthetic protocols for the introduction of the radioactive isotope into the species that will be administered to the subject (the "active pharmacophore"). Furthermore, the short isotope half-lives of the commonly used radiolabels often necessitates generation in a clinical setting, rather than an external production facility, therefore the method used to convert the source radioactive isotope into the active diagnostic/therapeutic radiolabel should ideally be suitable for non-specialists.

Accordingly, there is a need for improved radiolabels and methods of preparing radiolabels for use in clinical setting.

Therefore, at least one object is the provision of an improved radiolabel. A further at least one object is the provision of method of preparing an improved radiolabel.

SUMMARY

According to a first aspect of the invention there is presented a compound of formula I wherein M is a transition metal ion having 6 d-shell valence electrons, wherein X is a counter ion and n is the number of counterions such that the total charge of the compound of formula I is zero, and wherein L has formula II wherein $R^1$, $R^2$, $R^3$, $R^8$, $R^7$, $R^1$, $R^9$, $R^{10}$, $R^{13}$ and $R^{14}$ are independently H, $OR^{15}$, $OCOR^{15}$, $OC(O)OR^{15}$, $OP(O)(OR^{15})(OR^{16})$, $OP(O)R^{15}R^{16}$, $SR^{15}$, $SCOR^{15}$, $SC(O)OR^{15}$, $SP(O)(OR^{15})(OR^{16})$, $SP(O)R^{15}R^{16}$, $NR^{15}R^{16}$, $NR^{16}COR^{15}$, $NR^{16}CO_2R^{15}$ or $NR^{17}P(O)(OR^{15})(OR^{16})$.

wherein $R^4$ and $R^5$ are H or linked CH groups to form an N,N-phenanthroline ring, and/or $R^{11}$ and $R^{12}$ are H or linked CH groups to form an N,N-phenanthroline ring, wherein $R^{15}$, $R^{16}$ and $R^{17}$ are independently selected from H and $C_1$-$C_{10}$ alkyl, polyethylene glycol (PEG) and polyether groups, and wherein Z is selected from a chemical bond, acetylene, disubstituted phenylene, naphthalene, anthracene, pyrene or similar chemically rigid spacer.

Accordingly, each ring within formula II is a nitrogen containing heterocycle. Examples of suitable nitrogen containing heterocycles include pyridine, imidazole, pyrimidine, pyrazole, triazole and other azoles.

In a preferred embodiment, at least one of $R^3$, $R^6$, $R^{10}$ and $R^{13}$ are electron donating groups such as OH, $NR^{15}R^{16}$, or $OR^{15}$.

Whilst not wishing to be bound by theory, it is suggested by the inventors that the use of an electron donating group at any one of $R^3$, $R^6$, $R^{10}$ and $R^{13}$ may increase the ability of the N on the pyridine upon which the electron donating group has been added to bind to the metal ion M of the compound, thereby forming a more stable compound, or alter the redox potential to stabilise the kinetically inert oxidation state.

The identity of $R^1$-$R^{14}$ may improve the biological compatibility of the compound, influence the interactions with proteins and/or improve the pharmacokinetic profile. The identity of $R^{15}$, $R^{16}$ and $R^{17}$ may improve the biological compatibility of the compound, influence the interactions with proteins and/or improve the pharmacokinetic profile.

Typically, M is selected from cobalt(III), rhodium(III), iridium(III), iron(II), ruthenium(II), or osmium(II). M may be selected from cobalt(III), rhodium(III), iron(II), or iridium(III). In a preferred embodiment, M is cobalt (III), or iron(II).

Typically, X is a pharmaceutically acceptable counterion for the complex $[M_4L_6]^{p+}$. For example, X may be selected from the list of $NO_3^-$, $SO_4^{2-}$, $Cl^-$, $Br^-$, acetate, tosylate, tartrate, succinate, phosphate, oxalate, mesylate, maleate, malate, or citrate. For example, in embodiments where p is 12, where X has a charge of $2^-$, n may be 6, and where X has a single charge, n may be 12.

For example, in one embodiment, X may be $NO_3^-$ and n may be 12. In an alternative example, X may be $SO_4^{2-}$ and n may be 6.

Compounds according to formula I typically form a complex comprising a pseudo-tetrahedral arrangement of d6-metal ions with one ligand of formula II arranged along each edge of the tetrahedron. Typically, the two nitrogens of each bipyridine group of each ligand binds to a single metal ion such that each ligand of formula II binds to two metal ions. The cage may be either racemic or entantiomerically pure, homochiral or heterochiral.

It has been found that the complexes according to the present aspect of the invention comprise a cavity within which target species may be retained. Typically, the target species is an anionic target species. Accordingly, the compound may be configured to capture and retain an anionic target species. Whilst it is to be understood that the target species will be in a thermodynamic equilibrium between being retained within the compound of formula I and being outwith the compound of formula I, the target species typically is retained or is associated with the compound of formula I for a sufficient timescale for intended uses, such as therapeutic or diagnostic uses, for example.

In embodiments, the target species may be a radiolabel anion.

The target species may comprise a radioactive isotope which can be used for either medical imaging or therapy.

The radioactive isotope may be selected from the group carbon-11 ($^{11}C$), fluorine-18 ($^{18}F$), copper-64 ($^{64}Cu$), gallium-68 ($^{68}Ga$), zirconium-89 ($^{89}Zr$), gallium-67 ($^{67}Ga$), technetium-99m ($^{99m}Tc$), indium-111 ($^{111}In$), iodine-123 ($^{123}I$), iodine-124 ($^{124}I$), copper-67 ($^{67}Cu$), rhenium-186 ($^{186}Re$), rhenium-188 ($^{188}Re$), lutetium-177 ($^{177}Lu$), astatine-211 ($^{211}At$), bismuth-213 ($^{213}Bi$) and actinium-225 ($^{225}Ac$). The radioactive isotope may be selected from $^{18}F$, $^{64}Cu$, $^{99m}Tc$, $^{123}I$, $^{124}I$, $^{131}I$ or $^{188}Re$. Preferably, the radioactive isotope may be selected from the group $^{99m}Tc$, $^{188}Re$, and $^{18}F$.

The radioactive isotopes may be incorporated into anionic species such as anionic metal-halo-species, halo-species, metalloid-halo, or anionic oxo-, metal-oxo-, or metalloid-oxo species, for example. Preferably, the radioactive isotopes are incorporated into anionic oxo-species.

Accordingly, in embodiments where the radioactive isotope is a metal, the target species may be an oxide of the radioactive element. For example, the target species may be $^{99m}TcO_4^-$ or $^{188}ReO_4^-$. Alternatively, in embodiments where the radioactive element is non-metallic, the target species may comprise any radioisotope containing anion including a fluoride or carbon species, such as $[^{18}F]BF_4^-$, $[^{18}]ArBF_3^-$, $[^{18}F]FSO_3^-$, or $[^{18}F]PF_6^-$ In a further alternative embodiment where the radioactive element is $[^{18}F]$fluorine, the target species may comprise one or more $^{18}F$ moieties, such as $SO_3F^-$ or fluorodeoxyglucose (FDG). In some embodiments, the target species may be $[^{64}Cu]CuCl_4^{2-}$. The target species may be iodine or iodide $[^{123}I]I^-$, $[^{124}I]I^-$, or $[^{131}I]I^-$.

Preferably, the compound of the invention is configured to capture and retain the target species. The captured target species may be retained within the compound during any future use. For example, the compound plus target species may be used for clinical uses such as diagnosis or treatment of a subject, and the target species may be operable to perform the normal diagnostic function whilst being retained within the compound.

In some embodiments, one or more of the ligands L may comprise at least one targeting moiety. The one or more ligand L may comprise at least one binding moiety. Accordingly, the ligand may be according to formula (III), (III)

wherein each of $R^{18}$-$R^{23}$ is independently selected from H, $OR^{24}$, $OCOR^{24}$, $OC(O)OR^{24}$, $OP(O)(OR^{24})(OR^{25})$, $OP(O)R^{24}R^{25}$, $SR^{24}$, $SCOR^{24}$, $SC(O)OR^{24}$, $SP(O)(OR^{24})(OR^{25})$, $SP(O)R^{24}R^{25}$, $NR^{24}R^{25}$, $NR^{24}COR^{25}$, $NR^{24}CO_2R^{25}$ or $NR^{26}P(O)(OR^{24})(OR^{25})$, or —Y—$R^{27}$;

wherein each of $R^{24}$, $R^{25}$ and $R^{26}$ are independently selected from H and $C_1$-$C_{10}$ alkyl, polyethylene glycol (PEG) and polyether groups;

wherein Y is a chemical bond or a linker moiety;

wherein Z is selected from a chemical bond, acetylene, disubstituted phenylene, naphthalene, anthracene, pyrene or similar chemically rigid spacer, and wherein $R^{27}$ is a targeting moiety.

The at least one targeting moiety may be a binding moiety. For example, the targeting moiety may preferentially bind to a specific target. The targeting moiety may have a high affinity for a target site such that when administered, the compound binds to the target site via the targeting moiety. Accordingly, in embodiments where the compound comprises at least one ligand comprising at least one targeting moiety, the compound may bind to a target area comprising the specific target of the targeting moiety or binding moiety, thereby allowing the location of the compound to be controlled.

In some embodiments, one or more ligand L may comprise a peptide or protein. The peptide or protein may be a targeting moiety or a binding moiety. The peptide or protein may be connected directly to the ligand L. The peptide or protein may be connected to the ligand L via a linker.

In embodiments where Y is a linker moiety, the linker moiety may be a spacer to ensure that the target moiety is distanced from the ligand L such that the binding site of the targeting moiety is available to bind to the target. The linker moiety may be a polyether, a hydrocarbon chain, an amino acid sequence, an aryl group, a heterocycle or similar. In embodiments where the target moiety is a protein, the spacer may ensure that the protein is distanced from the ligand such that the protein may fold correctly and such that the binding site of the protein is available to bind to the target.

The linker moiety may be a chemical modification that facilitates the connection of the targeting moiety to the ligand. For example, Y may comprise a nucleophile that is configured to react with the targeting moiety to thereby connect the targeting moiety to the ligand. The nucleophile may be any one of amine, amide, hydrazine, nitrite, azide, hydroxyl, alkoxide, alcohol, carboxylate, thiol, thiolcarboxylic acids (RC(O)—S—), dithiocarbonates (RO—C(S)—S—) and dithiocarbamates (R2N—C(S)—S—), for example.

In some embodiments, the target moiety may be a small molecule, peptide, protein or antibody. Non-limiting examples of biological targets include the somatatostatin receptor (e.g. octreotide peptide), integrins (RGD based peptides), prostate specific membrane antigen (peptide), G-protein coupled receptors, and immune checkpoint targets (antibodies).

Further examples of targeting molecules include small molecule drugs, sugars, signalling proteins, nucleic acids and derivatives. PEG chains and protein binding groups can be included to prolong blood circulation and modify pharmacokinetics.

In some embodiments, L has formula IV

(IV)

wherein $R^{28}$, $R^{29}$, $R^{30}$, $R^{31}$, $R^{32}$, $R^{33}$, $R^{34}$ and $R^{35}$ are independently selected from H, $OR^{36}$, $OCOR^{36}$, $OC(O)OR^{36}$, $OP(O)(OR^{36})(OR^{37})$, $OP(O)R^{36}R^{37}$, $SR^{36}$, $SCOR^{36}$, $SC(O)OR^{36}$, $SP(O)(OR^{36})(OR^{37})$, $SP(O)R^{36}R^{37}$, $NR^{36}R^{37}$, $NR^{37}COR^{38}$, $NR^{37}CO_2R^{36}$ or $NR^{38}P(O)(OR^{36})(OR^{37})$;

wherein $R^{36}$, $R^{37}$ and $R^{38}$ are independently selected from H, $C_1$-$C_{10}$ alkyl, polyethylene glycol (PEG) and polyether groups.

In embodiments, one or more of $R^{29}$, $R^{30}$, $R^{33}$, and $R^{34}$ may be $OR^{36}$, $OCOR^{36}$, $OC(O)OR^{36}$, $OP(O)(OR^{36})(OR^{37})$, $OP(O)R^{36}R^{37}$, $SR^{36}$, $SCOR^{38}$, $SC(O)OR^{38}$, $SP(O)(OR^{36})(OR^{37})$, $SP(O)R^{36}R^{37}$, $NR^{36}R^{37}$, $NR^{37}COR^{36}$, $NR^{37}CO_2R^{36}$ or $NR^{38}P(O)(OR^{36})(OR^{37})$, and $R^{28}$, $R^{31}$, $R^{32}$, and $R^{35}$ may be H.

In some embodiments $R^{30}$, $R^{31}$, $R^{34}$ and $R^{35}$ are H and L is of formula V (V)

In a preferred embodiment, $R^{29}$ and $R^{33}$ may be selected from OH, $OR^{36}$, $OCOR^{36}$, $OC(O)OR^{36}$, $OP(O)(OR^{36})(OR^{37})$, $OP(O)R^{36}R^{37}$, $SR^{36}$, $SCOR^{36}$, $SC(O)OR^{36}$, $SP(O)(OR^{36})(OR^{37})$, $SP(O)R^{36}R^{37}$, $NR^{36}R^{37}$, $NR^{37}COR^{36}$, $NR^{37}CO_2R^{36}$ or $NR^{38}P(O)(OR^{38})(OR^{37})OH$, $NR^{38}R^{39}$, $OR^{38}$, $NHCOR^{38}$, $NHCOR^{38}$, or $OCOR^{38}$, and $R^{28}$ and $R^{32}$ are H.

In a preferred embodiment, $R^{29}$ and $R^{33}$ may be selected from $NR^{36}R^{37}$, $NR^{37}COR^{36}$, $NR^{37}CO_2R^{36}$ or $NR^{38}P(O)(OR^{36})(OR^{37})OH$, $NR^{38}R^{39}$, $NHCOR^{38}$, or $NHCOR^{38}$, and $R^{28}$ and $R^{32}$ are H.

In a further preferred embodiment, $R^{29}$ and $R^{33}$ are $NH_2$ and $R^{29}$ and $R^{32}$ are H.

In a preferred embodiment, $R^{28}$, $R^{29}$, $R^{32}$ and $R^{33}$ are H.

In a second aspect the invention extends to a compound according to formula VI;

[T⊂M₄L₆]·X$_n$ (VI)

wherein T is a species retained within the cavity of the compound according to formula I; and wherein L, M, X and n are as defined for the first aspect of the invention.

Typically, T is an anionic species comprising a radioactive isotope. The radioactive isotope may be selected from the group carbon-11 ($^{11}C$), fluorine-18 ($^{18}F$), copper-64 ($^{64}Cu$), gallium-68 ($^{68}Ga$), zirconium-89 ($^{89}Zr$), gallium-67 ($^{67}Ga$), technetium-99m ($^{99m}Tc$), indium-111 ($^{111}In$), copper-67 ($^{67}Cu$), iodine-123 ($^{123}I$), iodine-124 ($^{124}I$), iodine-131 ($^{131}I$), rhenium-186 ($^{186}Re$), rhenium-188 ($^{188}Re$), lutetium-177 ($^{177}Lu$), astatine-211 ($^{211}At$), and actinium-225 ($^{225}Ac$). Preferably, the radioactive isotope may be selected from the group $^{99m}Tc$, $^{188}Re$, $^{64}Cu$, and $^{18}F$. The radioactive isotope may be selected from the group $^{99m}Tc$, $^{188}Re$, and $^{18}F$.

T may be an anionic halo-species, metal-halo-species, anionic oxo-species, or metal-oxo-species, for example.

Accordingly, in embodiments where the radioactive isotope is a metal, T may be an oxide of the radioactive isotope. For example, T may be $^{99m}TcO_4^-$ or $^{188}ReO_4^-$. Alternatively, in embodiments where the radioactive isotope is non-metallic, T may comprise any radioisotope containing anion including a fluoride, such as $B^{18}F_4^-$ or $P^{18}F_6^-$. In a further alternative embodiment where the radioactive element is $^{18}F$, the target species may comprise one or more $^{18}F$ moieties, such as $SO_3F^-$ or fluorodeoxyglucose (FDG).

T is typically not covalently bonded to the compound of formula I. Rather, T is encapsulated by the compound of formula I. For example, T may be retained as a result of multiple weak non-covalent interactions, such as columbic and H-bonding, with a contribution from the hydrophobic effect.

Preferred and optional features of the first aspect of the invention are preferred and optional features of the second aspect of the invention.

In a third aspect the invention extends to a pharmaceutical composition comprising the compound of the second aspect of the invention and a pharmaceutically acceptable excipient, carrier, vehicle or diluent.

According to a fourth aspect of the invention there is provided a compound according to second aspect of the invention or a pharmaceutical composition according to the third aspect of the invention for use as a diagnostic marker or label.

The compound or pharmaceutical composition may be for use in vivo. The compound may be for use in vitro.

The compound or pharmaceutical composition may be used in imaging diagnostic techniques. The compound or pharmaceutical composition may be used in imaging biological processes or diseases. For example, the compound or pharmaceutical composition may be used in positron emission tomography (PET), or single-photon emission computed tomography (SPECT). Accordingly, the compound or pharmaceutical composition may be used to image blood flow in the heart, blood pool imaging, detection of whether a cancer has spread to bones or to look at blood flow in the brain, for example.

In embodiments where the compound or pharmaceutical composition comprises $^{99m}TcO_4^-$, the compound or pharmaceutical composition may be used in SPECT scans.

The invention extends in a fifth aspect to a method of preparing a compound according to formula I, the method comprising the steps:
  a. providing a first solution comprising transition metal ions M having 7 d-shell valence electrons, and a second solution comprising ligands L according to formula II;
  b. mixing the first solution with the second solution;
  c. oxidising the transition metal ions M in the resulting compound, such that the structure of the complex becomes fixed.

Typically, during step c. the transition metal ion is oxidised from having 7 d-shell valence electrons to having 6 d-shell valence electrons.

Preferably, the transition metal ions M provided in step a. of the present aspect is selected from cobalt(II), rhodium(II) or iridium(II), iron(I), ruthenium(I), osmium(I). In a preferred embodiment, M is cobalt (II).

One of the problems associated with self-assembled complexes for applications in drug and diagnostic delivery is in part demonstrating the encapsulation of interesting probes or pharmacophores, and more importantly, showing efficacy in vivo. In moving these interesting class of compounds from the laboratory towards the clinic, significant hurdles must be overcome. Most significantly, self-assembled cages and capsules known in the art utilize weak non-covalent or metal-ligand interactions that allows multicomponent, macromolecular species to form often in quantitative yield with 100% atom efficiency. However, it is the reversibility of these weak interactions that facilitates access to the globally most stable ensemble, which also presents the single largest problem. Unlike in the laboratory, where most investigations are carried out "at-equilibrium", moving such ensembles to a biological environment relevant to medical applications (where conditions such as very high dilution, numerous competing "ligands" etc must be tolerated) places the system far-away from where the intact assembly is thermodynamically preferred. Therefore bio-compatibility must be ensured through kinetic robustness. Utilizing self-assembled capsules and cages known in the art as inert carriers for clinically relevant species therefore necessitates the use of less dynamic interactions, making synthesis of these systems more challenging.

In contrast, it has been found that compounds of the invention comprising $Co^{II}$, for example, are labile and allow the ligands of the complex to bind and unbind to reach the most thermodynamically stable arrangement. However, when the $Co^{II}$ is oxidised to $Co^{III}$ in this example, the complex becomes much more stable and the ligands are bound more tightly to the cobalt ions. Accordingly, the arrangement of the ligands is stabilised and the replacement of one or more ligands with a competing ligand made more difficult.

As a result, the method of the present aspect of the invention allows the compound of formula I to be readily formed and then to be "fixed" by oxidising the metal ions. Therefore, a robust complex is produced that may withstand biological conditions, and as a result be suitable for medical applications. For example, the compound of formula I may be used in diagnostic methods, such as PET and SPECT scans.

The first solution comprising M may comprise any suitable salt of M. For example, in embodiments where M is in the 2+ oxidation state, M(II), the first solution may comprise $M(NO_3)_2$, $MCl_2$, $MBr_2$, $MSO_4$, $M_3(PO_4)_2$, etc.

In some embodiments, the metal ion salt may comprise anions that form the counterions $X_n$ of the compound of the invention.

Typically, the first solution and the second solution comprise an aqueous medium. The aqueous medium may be an aqueous solution. The aqueous solution may comprise additional salts and other species. The aqueous solution may comprise a buffering agent to stabilise the pH of the aqueous solution. For example, the aqueous solution may comprise a buffering agent that maintains the pH of the aqueous solution around neutral pH. The aqueous solution may comprise a buffering agent that maintains the pH of the aqueous solution around acidic pH. The aqueous solution may comprise a buffering agent that maintains the pH of the aqueous solution in alkaline pH.

M may be oxidised in step c. by an oxidising agent. The oxidising agent may be cerium ammonium nitrate. Alternatively, M may be oxidised by electrolysis or any other standard method of oxidation.

In some embodiments, the oxidising agent may be any single electron oxidant with suitable oxidation potential to affect conversion from, for example, cobalt(II) to cobalt(II).

Preferably, the compounds formed by the method of the present aspect of the invention are used to capture and retain radiolabels as described in the first and second aspects. For example, the radiolabels may be selected form the group $^{99m}TcO_4^-$, $^{188}ReO_4^-$, $[^{18}F]BF_4^-$, $[^{18}F]PF_6^-$, $[^{18}F]SO_3F^-$, or $[^{18}F]$-fluorodeoxyglucose (FDG).

Accordingly, the method may further comprise the step of adding a solution comprising a radiolabel with the compound of formula I to form a compound of formula VI. Typically, the compound of formula VI is formed by simple mixing of a solution with the radiolabel and a solution comprising the compound of formula I without requiring the formation of any covalent chemical bonds, thereby making the process simple and fast. As such, the method does not require any specialist radiochemistry training. Therefore, the method may be carried out in a clinical setting without requiring specialist equipment.

Typically, the method of the present aspect may be carried out in a clinical setting.

According to a sixth aspect of the invention, there Is provided a method of using the compound according to formula VI for diagnosis comprising the steps;
 providing a compound according to formula VI;
 administering the compound to a subject; and
 monitoring the location and/or movement of the compound within the subject.

The subject may be a mammal such as a human, a mouse, a rat, a dog, a cat, a horse, a pig, a cow, a sheep, a primate, etc. Preferably, the subject is a human.

The compound of formula VI may be administered intravenously, orally, subcutaneously, topically, pulmonary, intraarterially, intrathecally etc.

The radiolabel of the compound of formula VI may emit radiation that allows the location of the compound to be monitored.

In embodiments where the compound of formula VI comprises a targeting moiety, the compound of formula VI may target a specific type of cell or tissue and therefore, determination of the location of the radiolabel will determine the location of the specific type of cell or tissue.

The method of the present aspect may allow the flow of fluid within the body to be monitored. For example, the compound of formula VI or a pharmaceutical composition comprising the compound of formula VI may be injected into the blood stream of a subject and the flow of the compound through the blood vessels of the subject may allow the flow of blood through those vessels to be observed and monitored.

The method may correspond to a PET scan or a SPECT scan using the compound of formula VI to deliver the required radiolabel.

Preferred and optional features of the first to sixth aspects are preferred and optional features of the first to sixth aspects.

BRIEF DESCRIPTION OF THE FIGURES

Embodiments of the present invention will now be described, by way of non-limiting example, with reference to the accompanying drawings.

FIG. 1. (a) Chemical structure of inert $Co^{III}_4L_6$ nanocarrier systems (only one ligand out of six shown for clarity); (b) X-Ray crystal structure of $[ClO_4 \subset C1]^{11+}$, where C1 is $Co_4L^1_6$ and $L^1$ is of formula VI below. Associated anions and solvent molecules removed for clarity; (c) X-Ray crystal structure of $[ReO_4 \subset C2]^{11+}$, where C2 is $Co_4L^2_6$ and $L^2$ is of formula VII below. Associated anions and solvent molecules removed for clarity; (d) X-Ray crystal structure of $[CuCl_4 \subset Fe_4L^1_6]^{10+}$, where $L^1$ is of formula VI below. Associated anions and solvent molecules removed for clarity; (e) X-Ray crystal structure of $[PF_6 \subset Fe_4L^1_6]^{11+}$, where $L^1$ is of formula VI below. Associated anions and solvent molecules removed for clarity.

DETAILED DESCRIPTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The method of preparing the compositions of the invention combines the benefits of a dynamic self-assembly reaction, using bridging bidentate ligands and labile $d^7$ $Co^{II}$ ions, and yet is able to create multi-component ensembles with covalent-like robustness following simple oxidation ("Fixing") of the equilibrated species. We now demonstrate the real benefits of developing this method, showing that an inert, prototypical $Co^{III}_4L_6$ species can function in vivo as a generic nanocarrier system for radiolabelled anions, thus providing numerous opportunities in nuclear medicine and beyond.

Validating the in vivo use of these $Co^{III}$ capsule systems using the encapsulation of small radio-enriched anions presented several attractive features as well as opportunities. From a nuclear medicine perspective, labelling through non-covalent encapsulation is an underdeveloped approach, it also has the potential to address some of the key operational difficulties in this field. In particular, the short half-lives of many commonly used emitting isotopes have hampered the development of labelled bio-probes because of the difficulty in establishing simple synthetic procedures for use in a clinical setting. In contrast, non-covalent encapsulation is not only operationally simple it is also very rapid. This method also separates the bio-targeting and labelling technologies, wherein the interior of the cage that is responsible for hosting the radiolabel is distinct from the cage periphery, which can readily be decorated with different bio-targeting groups. This gives the potential to use a single technology platform for diagnosing and treating various disease states by encapsulating different radiolabelled species inside the same core-cage structure that is externally functionalised with different groups.

Example 1

Figure 1A:
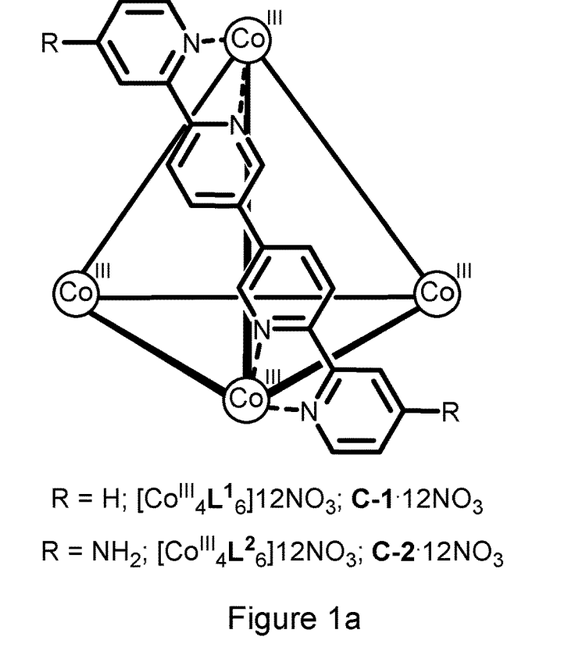

Initial investigations focused on the host-guest chemistry of the small tetrahedron $[Co^{III}_4L^1_6]^{12+}$, C1 (FIG. 1a), where $L^1$ is of formula VII.

(VII)

Figure 1B:
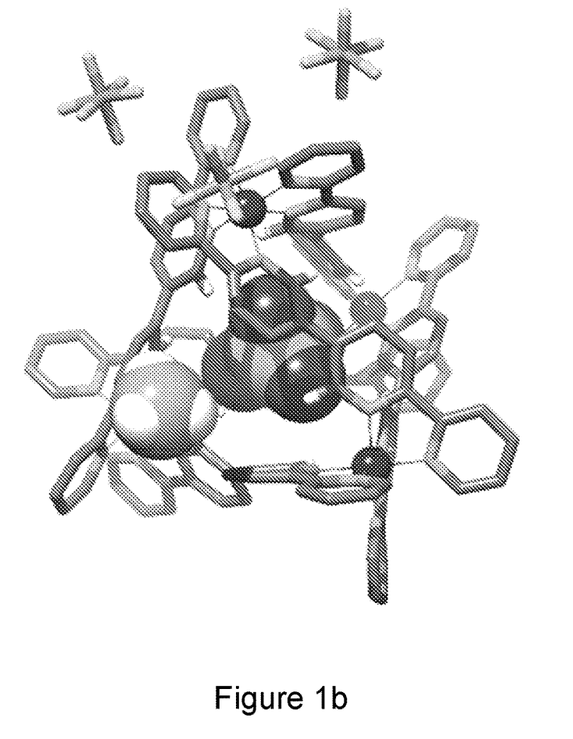
Figure 1C:
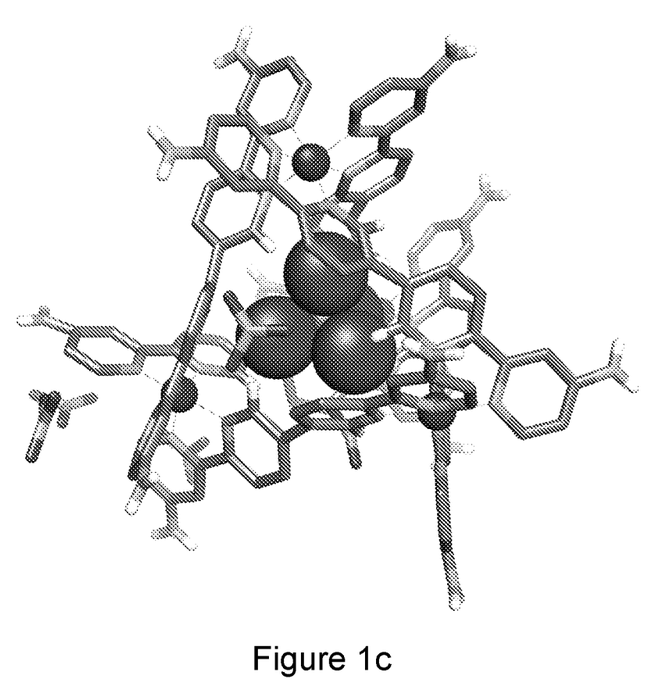
Figure 1D:
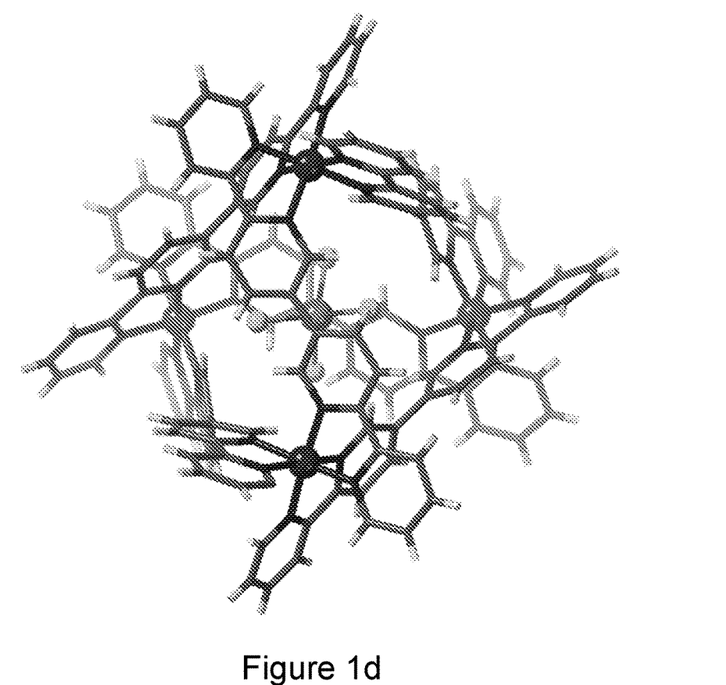
Figure 1E:
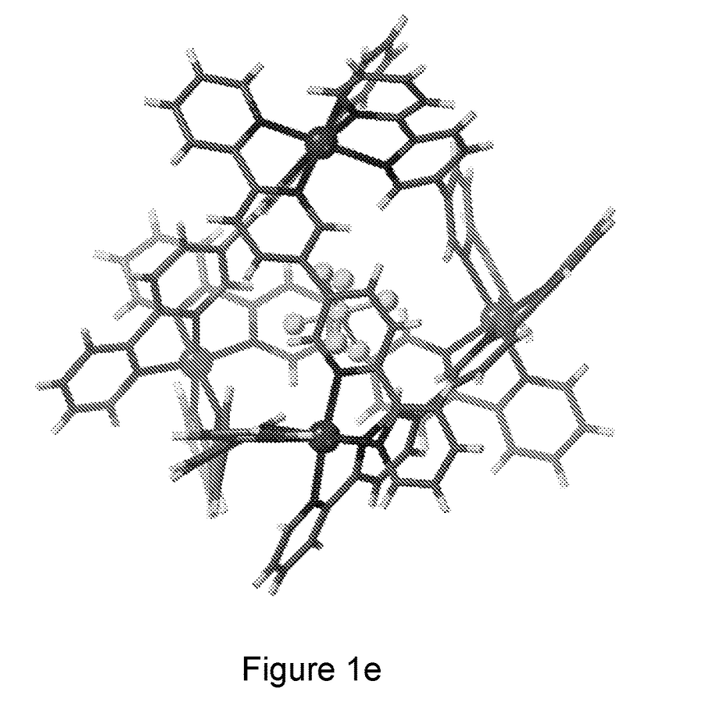
Figure 2:
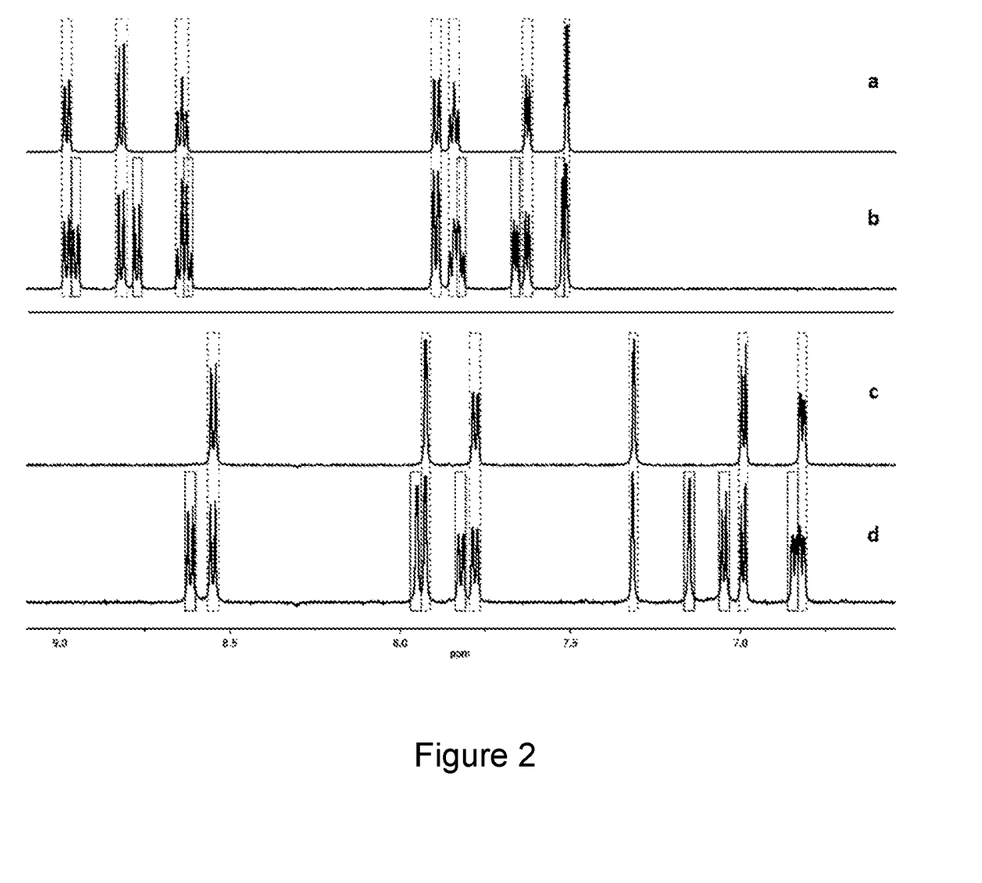
FIG. 2. $^1H$ NMR spectra (500 MHz, 298 K) showing the encapsulation of $ReO_4^-$ by C1 in $D_2O$. (a) C1·12$NO_3$ only; (b) C1·12$NO_3$+$NH_4ReO_4$; (c) C2·12$NO_3$ only; (d) C1·12$NO_3$+$NH_4ReO$ (free cage signals within lightly dashed boxes, occupied cage signals within heavily dashed boxes).

This novel compound was prepared using the "assembly-followed-by-fixing" method described below starting with the known ligand $L^1$. Furthermore, the synthesis from divalent $Co^{II}(NO_3)_2 \cdot 6H_2O$ and oxidized with cerium ammonium nitrate (CAN), resulted in a dodeca-nitrate salt, C1·12$NO_3$, obtained in 82% yield, that was directly soluble in water at concentrations in excess of 1 mM, thus negating the need to functionalize with aqueous-solubilizing groups. Molecular modelling also revealed that while the cavity size is relatively modest, 134 Å$^3$, this species should be able to accommodate a number of small anions within its interior, which was indeed the case. It was found that more "hydrophobic" anions bind best, with $PF_6^-$ giving the highest $K_a$ (68000 M$^{-1}$) while perrhenate $ReO_4^-$ also showed significant affinity (28000 M$^{-1}$; for details of $K_a$ determination, see below). Perrhenate binding is particularly easy to observe in solution as it is in slow exchange on the $^1H$ NMR timescale, with separate signals observable for both the empty and occupied capsule at sub-stoichiometric ratios (FIG. 2). Other anions such as $BF_4^-$, $ClO_4^-$ and even $SO_4^{2-}$ also bind, albeit more weakly, with association constants ranging from 100 M$^{-1}$ ($SO_4^{2-}$) to 7000 M$^{-1}$ ($ClO_4^-$). Considering other biological anions that might compete with a radio-enriched anion, we also looked at $PO_4^{3-}$ which showed no evidence of binding in $D_2O$. The encapsulation of $ClO_4^-$ has also been confirmed by X-ray crystallography (FIG. 1b) and more recently $ReO_4^-$ as well.

Figure 3:
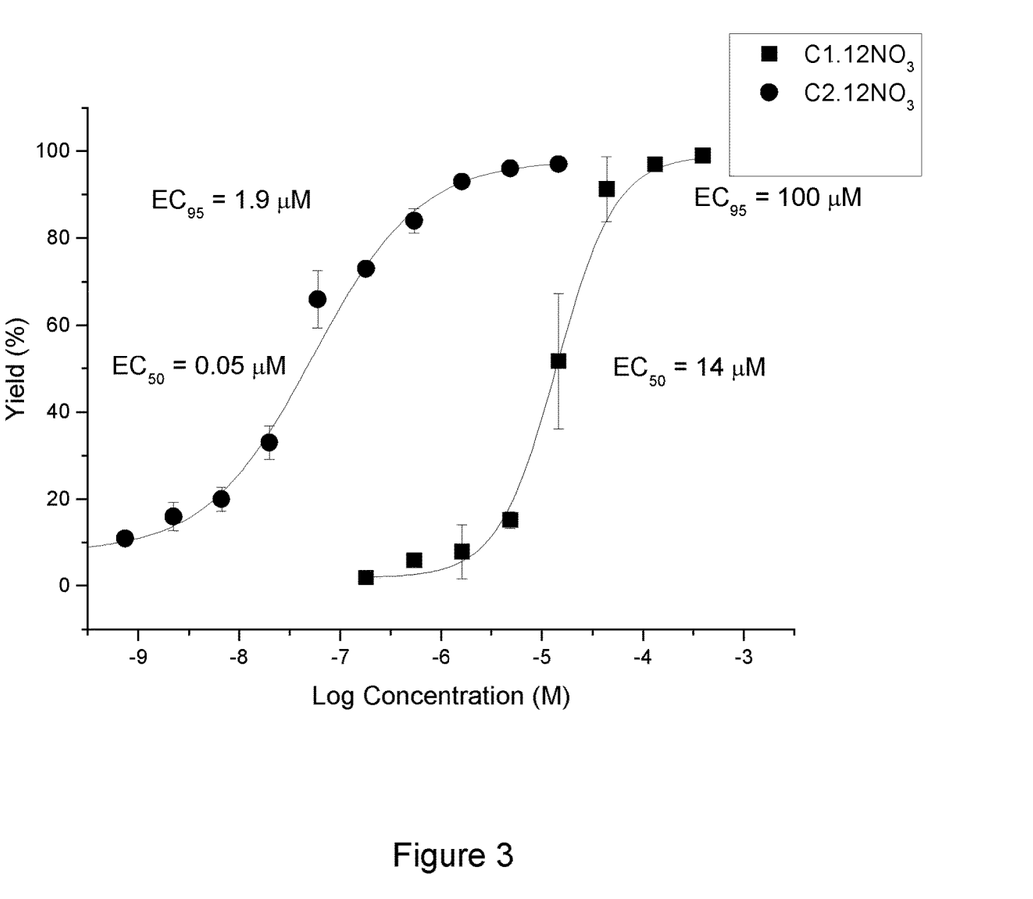
FIG. 3. Radiochemical yield for $^{99m}TcO_4^-$ for encapsulation as a function of cage concentration (C1, black squares; C2, black circles).

Moving our attention to the encapsulation of radioenriched anions, while $[^{18}F]BF_4^-$ and $[^{18}F]PF_6^-$ present opportunities for Positron Emission Tomography (PET) imaging, we decided to focus on the gamma-emitting $^{99m}TcO_4^-$ anion as both isostructural $ClO_4^-$ and $ReO_4^-$ anions bind to C1. The use of enriched pertechnatate also does not require any prior radiochemistry as it is available direct from a source Mo generator, therefore ideal for validating this non-covalent approach to radiochemical encapsulation. We started by investigating the concentrations of C1 required to give quantitative radiochemical yield (>95%) of encapsulated $^{99m}TcO_4^-$ species, as this would determine the dose of cage compound administered to a subject in any subsequent in vivo imaging experiments. The best way to assess this was found to be using thin layer chromatography (TLC) on standard phase silica gel; while unencapsulated $^{99m}TcO_4^-$ elutes in water with the solvent front, the encapsulated $[^{99m}TcO_4 \subset C1]^{11+}$ is retained on the baseline. The % radiochemical yield could therefore be easily calculated by comparing and the radioactive counts associated with solvent front and baseline of cut TLC plates using a Wizard automatic gamma counter (Perkin Elmer). Using this method it was found that full encapsulation could be achieved at 100 µM C1, with an $EC_{50}$ (i.e. concentration required for 50% encapsulation) value of 14 µM (FIG. 3, black squares). These preliminary experiments also showed that, as anticipated, labelling the cage compound through encapsulation is extremely facile and rapid, with the radiochemical yields invariant of mixing time, with 5 minutes giving the same yield as hours.

Figure 4:
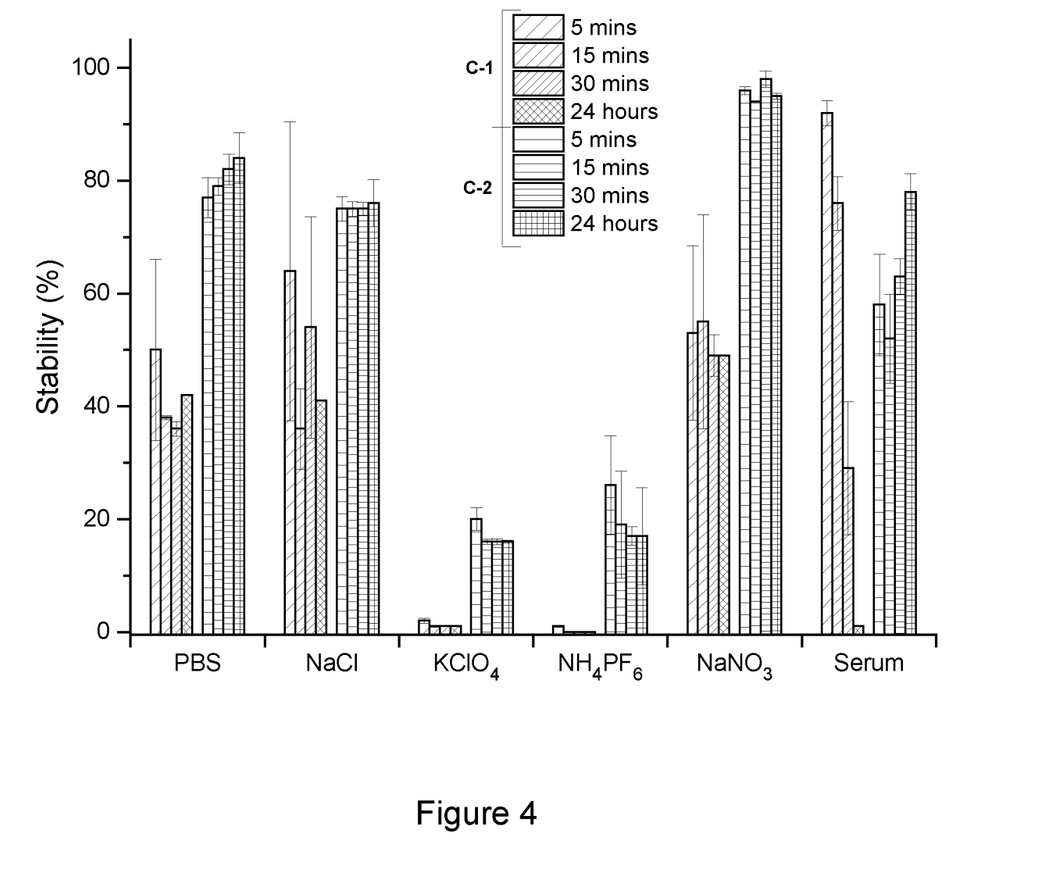
FIG. 4. Stability of encapsulated complexes to a range of different anions and conditions.

Next the radiochemical yield was similarly assessed under a range of conditions designed to probe the stability of the encapsulated species (FIG. 4, diagonal bars). As can be seen the radiochemical yield is maintained at a good level (40-60%) in the presence of a large excess of competing $NO_3^-$, $Cl^-$ and $PO_4^{2-/3-}$ anions relevant to in vivo use, neither does this diminish as a function of time. In contrast, when anions which are known to bind to the cavity of C1 (i.e. $ClO_4^-$ and $PF_6^-$) were added to the sample of prior to mixing with $^{99m}TcO_4$, then the radiochemical yield reduced dramatically to trace levels. While neither $ClO_4^-$; and $PF_6^-$ represent concerns from an in vivo perspective, both clearly demonstrate that a high radiochemical yield is a result of encapsulation rather than simple ion pairing with the cage periphery. These experiments also show that the equilibrated samples are stable, showing neither an increase or decrease in radiochemical yield as a function of time. In contrast when the same encapsulation experiment was carried out in serum, very good radiochemical yields were obtained immediately after mixing, however, after leaving the sample for just 30 minutes a value of over 90% had dropped to less than 30%, and after 24 hours this had diminished to trace levels. As the encapsulation process takes place on a much shorter timeframe, as evidenced by the rapid uptake and displacement of $^{99m}TcO_4$ in the presence of competing anions, we attribute this slower change to probable cage decomposition, and with it release of the enriched anion.

Example 2

The diamino substituted ligand, $L^2$ of formula VIII, was synthesised in several steps, starting from 2-bromopyridine-N-oxide by Pd-catalysed coupling with 5-Bromo-2-(tributylstannyl)pyridine, followed by simultaneous reduction of nitro and N-oxide groups and then Ni catalysed homocoupling (See supplementary materials for details). The difference in the ligand "strength" immediately became apparent from subsequent "assembly-followed-by-fixing" reactions, in particular the self-assembly part of this method required prolonged heating to equilibrate, furthermore, following oxidation we always obtained a mixture of C2 $(Co_4L^2_6)^{12+}$ and the corresponding helicate, $[Co^{III}_2L^2_3]^{6+}$, which we attribute to probable kinetic trapping in the assembly phase of the reaction. Nonetheless, we could separate from the smaller species using size-exclusion chromatography, which gave a pure sample of C2·12NO_3 in 14% yield.

(VIII)

It is suggested that cage disassembly could be triggered by partial reduction of the $Co^{III}$ centers in the presence of biological reducing groups (e.g. disulfides etc.), which would then lower the energy barrier to subsequent ligand exchange with various species. Therefore, the stronger σ-donor ligand $L^2$ may stabilize the higher oxidation state of the Co. In addition, if in situ reduction of the cage compound was not occurring, rather just decomposition caused by direct ligand substitution with the $Co^{III}$ state, then the increased donor strength of the $L^2$ ligand set may also aid in vivo stability.

Returning to radiochemical labelling experiments, substitution of the cage structure with 12 amino groups had an unforeseen yet very positive impact on $^{99m}TcO_4^-$ encapsulation. In the absence of any competing anions it was observed that the concentration of cage required to achieve >95% radiochemical yield was reduced nearly 50 fold to 1.9 µM, with an $EC_{50}$ value of just 0.05 µM (FIG. 3, black circles). Furthermore, repeating the same anion stability experiments as originally tested with C1, also appeared to show that this increase in affinity is specific to $^{99m}TcO_4^-$, as all the other anionic species appear to reduce the radiochemical yield less significantly (FIG. 4, C2 24 hrs). When the same radiochemical labelling experiment was performed in the presence of serum, no real drop in radiochemical yield was observed after even 24 hours, indicating that the amino groups have the desired effect of increasing the cage's kinetic robustness.

Figure 5:
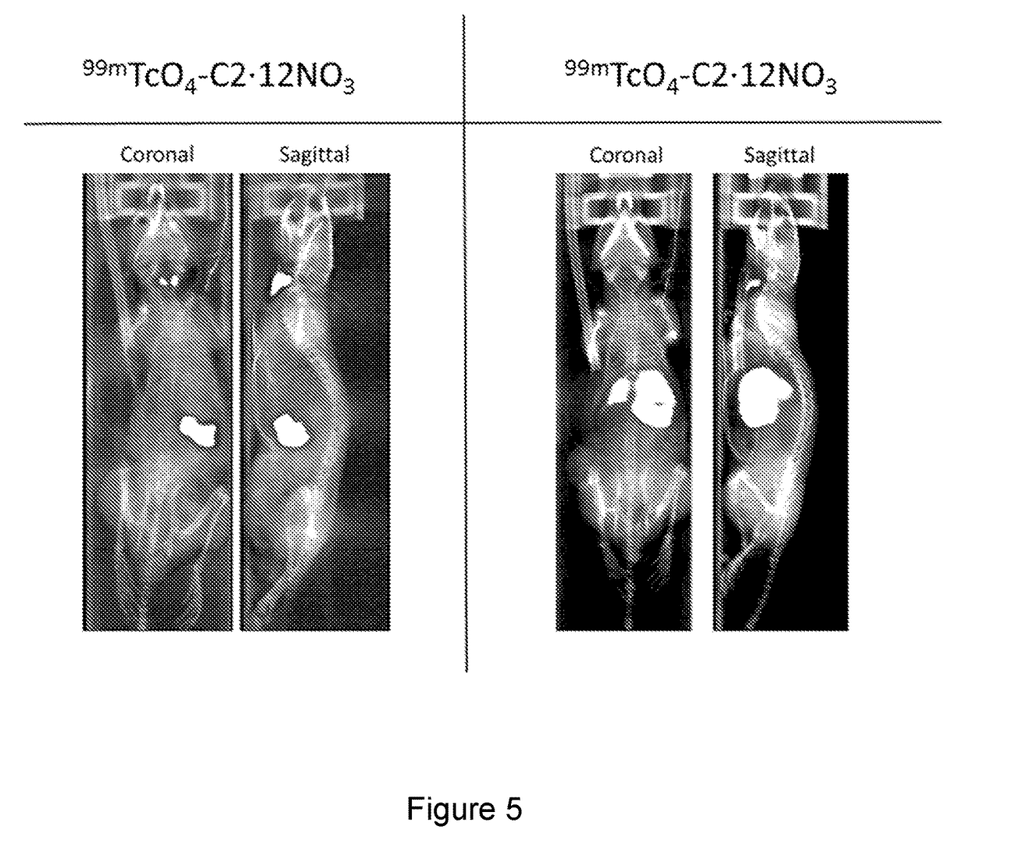
FIG. 5: SPECT/CT images showing the comparison of "free" $[^{99m}Tc]TcO_4^-$ uptake in naïve animals vs. nanocarrier encapsulated $[^{99m}Tc]TcO_4^-$.

In light of the improved stability in serum, as well as the lower dose required to fully encapsulate $^{99m}TcO_4^-$, C2 was selected to take forward for Single-Photon Emission Computed Tomography (SPECT) imaging experiments. Furthermore, MTT assays also revealed low to moderate cytotoxicity ($EC_{50}$=10.6 µM, see below) suggesting that this compound should be safe for in vivo use at the concentration levels needed for non-covalent labelling. The biodistribution of free $^{99m}TcO_4^-$ is well understood, with this small anion known to localise in the thyroid, lungs, stomach and liver. It can be used to study disruption of the blood brain barrier as it will not accumulate significantly in the brain if the blood brain barrier is intact. It binds weakly to plasma proteins and clears in ca. 30 mins. It is excreted in both urine and faeces hence can be detected in both kidneys and small intestine prior to excretion (FIG. 5a). In contrast, when the same dose of $^{99m}TcO_4^-$ was administered in the presence of 1 mg/kg C2·12NO_3, it was clearly observable that the cage compound markedly affects the bio-distribution of this label (FIG. 5).

Discussion

What is important to take away from these experiments is not where the $^{99m}TcO_4^-$ anion localizes in the presence of C2, but rather the significant change compared to the free anion alone. The use of a non-covalent encapsulation approach also provides compelling evidence that the capsule remains intact during imaging, as disassembly would remove the well-defined cavity and with it the significant affinity that is required to keep the anion associated in the presence of vast excess of many other competing biological cations.

Accordingly, the exemplified radiolabels are stable in biological conditions for the time-frames of typical radiolabel diagnostic techniques, and can be created readily in a clinical, rather than laboratory setting.

Synthesis of Ligands

Fragments 5-bromo-2,2'-bipyridine and 5-Bromo-2-(tributylstannyl)pyridine were synthesised according to a literature procedure.

5-(5-bipyrdin-2,2'-yl)-2,2'-bipyridine ($L^1$)

A solution of nickel chloride (0.174 g, 1.34 mmol) and triphenylphosphine (1.34 g, 5.10 mmol) in N,N-dimethylformamide (12.0 mL) was heated at 50° C. for 0.5 h under $N_2$. The resulting blue suspension was treated with zinc dust (0.0903 g. 1.38 mmol) to produce a red brown suspension after 0.5 h, to which 5-bromo-2,2'-bipyridine (0.299 g, 1.27 mmol) in N,N-dimethylformamide (6.0 mL) was added and the mixture stirred at RT for 3 d. To this, $Na_2EDTA$ (0.25 M, 60 mL, 15.0 mmol) was added and the aqueous layer washed with dichloromethane (5×100 mL) and brine added (20 mL). The combined organic layers were dried over $MgSO_4$, the solvent removed in vacuo and purified by silica flash column (1% triethylamine, 1% methanol in dichloromethane). This was recrystallised in hot acetonitrile to give white plate crystals. Yield=0.126 g (64%).

m.p. 233-235° C. $^1H$ NMR (600 MHz, $CDCl_3$): δ 9.03 (dd, J=2.4, 0.8 Hz, 2H, $H_G$), 8.75 (d, J=4.8 Hz, 2H, $H_A$), 8.58 (dd, J=8.3, 0.8 Hz, 2H, $H_E$), 8.50 (d, J=8.0 Hz, 2H, $H_D$), 8.13 (dd, J=8.2, 2.4 Hz, 2H, $H_F$), 7.89 (t, J=7.7 Hz, 2H, $H_C$), 7.38 (dd, J=7.5, 4.8 Hz, 2H, $H_B$). $^{13}C$ NMR (151 MHz, $CDCl_3$): δ 155.8, 155.6, 149.3, 147.5, 137.0, 135.2, 133.1, 124.0, 121.2, 121.2. HR-ESI: m/z 311.12890 (predicted $[M+H]^+$=311.12912), 333.11180 (predicted $[M+Na]^+$=333.11107).

5'-bromo-4-nitro-(2,2'-bipyridine)-N-oxide 2-bromo-4-nitropyridine N-oxide (4.039 g, 18.4 mmol), palladium tetrakis(triphenylphosphine) (1.04 g, 0.901 mmol) and 5-Bromo-2-(tributylstannyl)pyridine (8.29 g. 18.5 mmol) were combined in toluene (80 mL) and heated at 100° C. for 24 h under $N_2$. The mixture was allowed to cool to room temperature, diluted with dichloromethane (30 mL) and filtered. The solvent was removed from filtrate in vacuo. The crude product was recrystallised from hot ethanol and then purified by silica flash column (gradient: dichloromethane to dichloromethane 4% diethylether) to give a colourless powder. Yield=3.07 g (57%).

$^1H$ NMR (500 MHz, Chloroform-d) δ 9.19 (d, J=3.3 Hz, 1H, $H_F$), 8.90 (dd, J=8.7, 0.7 Hz, 1H, $H_A$), 8.84 (dd, J=2.4, 0.7 Hz, 1H, $H_C$), 8.35 (d, J=7.2 Hz, 1H, $H_D$), 8.08 (dd, J=7.2, 3.3 Hz, 1H, $H_E$), 8.01 (dd, J=8.6, 2.4 Hz, 1H, $H_B$). $^{13}C$ NMR (128 MHz, Chloroform-d) δ 151.13, 147.58, 146.03, 142.65, 142.25, 139.47, 126.15, 122.94, 122.54, 119.19. HR-ESI: m/z 295.96780 (predicted $[M+H]^+$=295.96653), 317.9480 (predicted $[M+Na]^+$=317.94847).

5'-bromo-(2,2'-bipyridin)-4-amine 5-bromo-4'-nitro-2,2'-bipyridine N-oxide (1.66 g, 5.60 mmol) and iron (1.67 g, 29.9 mmol) were combined in acetic acid (50 mL) and heated at 100° C. for 3 h under $N_2$. The mixture was allowed to cool to room temperature and a solution of NaOH (10.5456 g, 0.268 mol), $Na_2EDTA$ (17.564 g, 60.1 mmol) in water (50 mL) and ammonium hydroxide solution (30%, 100 mL) was added slowly. The mixture was then extracted with chloroform (3×150 mL) and the combined organic phases were dried over $MgSO_4$. The solvent was removed in vacuo and the crude product was recrystallised from hot toluene to give colourless needle crystals. Yield=1.03 g (74%).

$^1H$ NMR (600 MHz, Chloroform-d) δ 8.68 (d, J=2.4 Hz, 1H, $H_G$), 8.32-8.25 (m, 2H, $H_{A,E}$), 7.91 (dd, J=8.5, 2.4 Hz, 1H, $H_F$), 7.64 (d, J=2.5, 0.5 Hz, 1H, $H_D$), 6.57 (dd, J=5.5, 2.4 Hz, 1H, $H_B$), 4.24 (s, 2H, $H_C$). $^{13}C$ NMR (126 MHz, Chloroform-d) δ 155.98, 155.02, 153.74, 150.07, 139.56, 122.62, 121.06, 110.00, 106.88. HR-ESI: m/z 249.99910 (predicted $[M+H]^+$=249.99744).

5'-(4'-amino-(2,2'-bipyridin)-5-yl)-(2,2'-bipyridin)-4-amine (L)

Nickel chloride (157 mg, 1.21 mmol) and triphenylphosphine (218 mg, 1.92 mmol) were combined in in N,N-dimethylformamide (10 mL) and heated at 50° C. for 1 h under $N_2$. The resulting blue suspension was treated with zinc dust (155 mg, 2.37 mmol) to produce a red brown suspension after 0.5 h, to which 5′-bromo-(2,2′-bipyridin)-4-amine (298 mg, 1.20 mmol) in N,N-dimethylformamide (5 mL) was added and the mixture stirred at RT for 3 d. A solution of $Na_2EDTA$ (3.52 g, 12.0 mmol) and NaOH (1.89 g, 48.0 mmol) in ammonium hydroxide solution (30%, 20 mL) was added to the mixture and it was heated at 50° C. for 24 h. The colourless precipitate was collected by filtration and dissolved in tetrahydrofuran, filtered and the solvent removed in vacuo. The crude product was recrystallised from hot acetonitrile to give colourless powder. Yield=151 mg (37%).

342° C. decomposition $^1H$ NMR (500 MHz, DMSO-d) δ 9.09 (dd, J=2.4, 0.8 Hz, 1H, $H_G$), 8.45 (dd, J=8.3, 0.8 Hz, 1H, $H_E$), 8.33 (dd, J=8.3, 2.4 HZ, 1H, $H_F$), 8.15 (d, J=5.5 Hz, 1H, $H_A$), 7.70 (d, J=2.3 Hz, 1H, $H_D$) 6.56 (dd, J=5.5, 2.3 Hz, 1H, $H_B$), 6.21 (s, 2H, $H_C$). $^{13}C$ NMR (126 MHz, DMSO-d) δ 155.67, 155.20, 154.82, 149.37, 146.97, 134.83, 132.03, 120.36, 109.14, 105.61. HR-ESI: m/z 341.15240 (predicted $[M+H]^+$=341.15092), 363.1339 (predicted $[M+Na]^+$=363.1334).

Synthesis of $[Co_4L_6]^{12+}$ species $Co_4(L^1)_6(NO_3)_{12}$

Cobalt nitrate hexahydrate (0.0211 g, 72.5 µmol) and $L^1$ (0.0337 g, 109 µmol) were suspended in a mixture of degassed water-acetonitrile (9:1, 5.0 mL) and heated at 50° C. for 15 h under $N_2$. The reaction was cooled to room temperature before cerium(IV) ammonium nitrate (0.0598 g, 109 µmol) in acetonitrile (6.6 mL) was added via syringe pump (6 µL min$^{-1}$, 18 h). Dilution with acetonitrile (8.0 mL) was required to precipitate the product, which was isolated by filtration onto celite and washed with acetonitrile. This was eluted with water and the solution was freeze-dried to give the compound as a yellow solid. Yield=0.0420 g (82%).

$^1H$ NMR (500 MHz, $D_2O$): δ 8.97 (d, J=8.1 Hz, 12H, $H_D$), 8.81 (d, J=8.4 Hz, 12H, $H_B$), 8.62 (dd, J=8.1, 7.0 Hz, 12H, $H_C$), 7.91 (d, J=8.4 Hz, 12H, $H_F$), 7.83 (dd, J=7.0, 6.0 Hz, 12H, $H_B$), 7.62 (d, J=6.0 Hz, 12H, $H_A$), 7.50 (s, 12H, $H_G$). $^{13}C$ NMR (126 MHz, D2O): δ 155.8, 154.6, 151.7, 149.2, 144.5, 144.5 138.2, 131.8, 127.9, 126.5. $^1H$ DOSY NMR (500 MHz, $D_2O$): D=2.17×10-6 cm$^2$ s$^{-1}$; calculated hydrodynamic radius=11.3 Å. ESI-MS (m/z): 885 (3+), 648 (4+), 344 (7+), 293 (8+).

$Co_4(L^2)_6(NO_3)_{12}$

Cobalt nitrate hexahydrate (17.2 mg, 59.1 µmol) and $L^2$ (30.1 mg, 88.4 µmol) were suspended in a mixture of degassed water-acetonitrile (9:1, 4 mL) and heated in a microwave reactor for 2 h at 80° C. The reaction was cooled to room temperature before cerium(IV) ammonium nitrate (501 mg, 91.4 µmol) in acetonitrile (4 mL) was added via syringe pump (4.2 µLmin$^{-1}$). Dilution with acetonitrile (40 mL) was required to cause precipitation, this was collected by filtration onto celite and washed with acetonitrile. The crude product was eluted with water and freeze dried to give an orange solid. It was then purified by size exclusion chromatography on sephadex LH-20 gel in water and freeze-dried to give an orange solid. Yield=6.1 mg (14%).

In an alternative method, $L^2$ (28.4 mg, 83.4 µmol) was suspended in a solution of C1 (20.2 mg, 7.04 µmol) in degassed acetonitrile (9:1, 3.9 mL), an aqueous solution of cobalt nitrate hexahydrate (2 mM, 141 µL) was added, the mixture sparged with $N_2$ and heated at 75° C. in a sealed vial. The mixture was allowed to cool, filtered through celite and the retentate washed with water (5 mL). The filtrate was freeze-dried, redissolved in water (2 mL) and purified by size exclusion chromatography on sephadex LH20 and freeze-dried to give an orange solid. Yield=11.9 mg, 56%). Characterisation identical to previous method.

$^1H$ NMR (600 MHz, $D_2O$) δ 8.55 (d, J=8.4 Hz, 12H, $H_D$), 7.92 (d, J=2.7 Hz, 12H, $H_C$), 7.78 (dd, J=8.3, 1.8 Hz, 12H, $H_B$), 7.31 (d, J=1.6 Hz, 12H, $H_F$), 6.99 (d, J=7.0 Hz, 12H, $H_A$) 6.81 (dd, J=7.0, 2.7 Hz, 12H, $H_B$). $^{13}C$ NMR (126 MHz, $D_2O$) δ 158.37, 156.49, 153.36, 148.46, 143.17, 137.28, 124.58, 114.68, 111.97, 109.99. $^1H$ DOSY NMR (500 MHz, $D_2O$): D=2.14×10-6 cm$^2$ s$^{-1}$; calculated hydrodynamic radius=11.5 Å. ESI-MS ESI-MS (m/z): 369.5 (7+), 315.6 (8+).

"Cold" Anion Binding Experiments: Determination of Association Constants ($K_B$)

$K_B$ for cage and guest combinations determined through $^1H$ NMR titration in unbuffered $D_2O$. A solution of compounds C1 or C2 with a guest compound was titrated into a solution of C1 or C2, thereby maintaining a constant concentration of C1 or C2.

Fast Exchange Determination

All observable shifts in the $^1H$ NMR spectra had their peak position plotted against concentration of guest. A global non-linear curve fitting function was then applied to the combined plots using the 1:1 binding model given by:

$$y = y_0 + \Delta y\left(\frac{(1 + K_a(P + x)) - \sqrt{(1 + K_a(P + x))^2 - 4K_aK_aPx}}{2K_aP}\right)$$

$y_0$=peak position with no guest
$\Delta y$=peak position with 100% bound
x=concentration of guest
P=concentration of cage Origin Function=$y=y_0+DY*((1+Ka*(P+x))-\text{sqrt}(((1+Ka*(P+x))^2-4*Ka*Ka*P*x))/(2*Ka*P)$ Slow Exchange Determination Concentration of guest ⊂ C1 or guest ⊂ C2 was calculated from $^1$H NMR integrals and plotted against guest concentration. A non-linear curve fitting function was then applied to the plot using the 1:1 binding model given by:

$$y = \frac{\left(x+P+\left(\frac{1}{K_a}\right)\right) + \sqrt{\left(x+P+\left(\frac{1}{K_a}\right)\right)^2 - (4Px)}}{2}$$

x=concentration of guest
y=Concentration of host guest complex
P=concentration of host Origin function=$((x+h+(1/K))-((x+h+(1/K))^2(4*h*x))^{(1/2)})/2$ The resulting binding constants of some example anions are provided in Table 1 below:

TABLE 1

Binding constants of various anions in unbuffered D$_2$O. Errors are estimated to be less than 10%.

| Guest | Formula | C1 (M$^{-1}$) | C2 (M$^{-1}$) |
|---|---|---|---|
| Sulfate | [SO$_4$] | 100 | |
| Tetrafluoroborate | [BF$_4$] | 500 | |
| Perchlorate | [ClO$_4$] | 7100 | 21000 |
| Hexafluorophosphate | [PF$_6$] | 61000 | |
| Perrhennate | [ReO$_4$] | 20000 | 22000 |

Cage Cytotoxicity Experiments: MTT Assays

HeLa cells were plated onto a 96-well plate in Dulbecco's Modified Eagle Medium (DMEM) (10% in PBS) (volume) at approximately 8000 cells/mL. The plate was incubated for 20 h to allow equilibrium. The DMEM was removed and replaced with fresh DMEM (100 μL) containing the compound being investigated, at the appropriate concentration; each concentration was added to seven wells. The plate was incubated for another 20 h before the removal of medium and washing of the cells with PBS. Then a 1.2 mM solution 3-[4,5-dimethylthiazol-2-yl]-2,5-diphenyl-2H tetrazolium bromide (5 mg) in media/PBS (7/3, 10 mL) was prepared and 100 μL added to each well. This was incubated for 3 h, at which point crystals were apparent. A solubilising solution (prepared: 5 mL Triton-X 100, 45 mL Isopropanol, 1 drop HCl (12M)) (100 μL) was added and the plate shaken on a plate shaker overnight to ensure complete dissolution of crystals. UV-visible absorbance measurements were carried out at 490 nm. For each concentration of the added compound the absorbances were averaged (discarding those more than two standard deviations from the mean). The absorbances were then normalised against that of the control cells. The resulting concentrations are shown in Table 2 below.

TABLE 2

Cytotoxic concentration for ligands C1 and C2

| Cytotoxicity values | C1 (μM) | C2 (μM) |
|---|---|---|
| Cytotoxic concentration 50% (CC$_{50}$) | 31.4 | 10.6 |

Pertechnetate Binding Experiments $^{99m}$TcO$_4$ was eluted from a 2.15 GBq Ultra-TechneKow™ DTE $^{99}$Mo/$^{99m}$Tc generator (Mallinckrodt. UK) in 4 mL 0.9% saline solution. $^{99m}$TcO$_4^-$ (1 μL, 1 MBq) was then added to C1 or C2 solutions (100 μl) and incubated at room temperature for 5 minutes. Pertechnetate encapsulation was assessed by silica gel thin layer chromatography, wherein eluting with DI water separates free $^{99m}$TcO$_4^-$, which runs with the solvent front, while bound $^{99m}$TcO$_4$ complex remains on the baseline. The proportion of bound and free $^{99m}$TcO$_4$ was determined by cutting the eluted TLCs into strips and independently analysing using a Wallac 1480 Wizard 3" automatic-gamma-counter (Perkin Elmer, USA). All reactions were carried out in DI water. The results are shown in FIG. 3.

Radiochemical stability was tested under a range of different salt conditions. In a typical experiment, $^{99m}$TcO$_4^-$ (1 μL, 1 MBq) was added to C1 or C2 solutions (50 μl, 132 μM) and incubated at room temperature for 5 minutes. Salt solutions (50 μl, 0.1 mM) were added and incubated at room temperature for 24 hours with aliquots taken at the stated time points and then analysed by the method described above (e.g. running on TLC followed detection using gamma counter).

In Vivo Imaging Experiments

Mice were injected iv with 25-35 MBq of $^{99m}$TcO$_4^-$ and 19 MBq of caged $^{99m}$TcO$_4$ under anaesthesia before being transferred to a temperature-controlled imaging bed and attached to an anaesthetic facemask (Minerve, France). $^{99m}$TcO$_4^-$ SPECT images (shown in FIG. 4) were acquired at ~40 minutes pi for 30 min under anaesthesia, whereas $^{99m}$TcO$_4 ⊂ $NH$_2$ SPECT images were acquired at 20 minutes pi for 100 min. In both cases SPECT was followed by CT scan (240 projections with 1 s exposure to 55 kVp X-rays). SPECT and CT Images (FIG. 5) were reconstructed with an iterative algorithm (HiSPECT, Scivis GmbH, Germany) and with exact cone beam Filtered Back Projection (VivoQuant, inviCRO LLC, USA), respectively.

The invention claimed is:

1. A compound of formula I wherein M is a transition metal ion having 6 d-shell valence electrons;

wherein X is a counter ion and n is the number of counterions such that the total charge of the compound of formula I is zero; and wherein L has formula II wherein $R^1$, $R^2$, $R^3$, $R^6$, $R^7$, $R^8$, $R^9$, $R^{10}$, $R^{13}$ and $R^{14}$ are independently H, $OR^{15}$, $OCOR^{15}$, $OC(O)OR^{15}$, $OP(O)(OR^{15})(OR^{16})$, $OP(O)R^{15}R^{16}$, $SR^{15}$, $SCOR^{15}$, $SC(O)OR^{15}$, $SP(O)(OR^{15})(OR^{16})$, $SP(O)R^{15}R^{16}$, $NR^{15}R^{16}$, $NR^{16}COR^{15}$, $NR^{16}CO_2R^{15}$ or $NR^{17}P(O)(OR^{15})(OR^{16})$;

wherein at least one of $R^3$, $R^6$, $R^{10}$ and $R^{13}$ are selected from the group OH, $NR^{15}R^{16}$ or $OR^{15}$;

wherein $R^4$ and $R^5$ are H or linked CH groups to form an N, N-phenanthroline ring, and $R^{11}$ and $R^{12}$ are H or linked CH groups to form an N,N-phenanthroline ring;

wherein $R^{15}$, $R^{16}$ and $R^{17}$ are independently selected from H and $C_1$-$C_{10}$ alkyl, polyethylene glycol (PEG) and polyether groups; and wherein Z is selected from a chemical bond, acetylene, disubstituted phenylene, naphthalene, anthracene, or pyrene.

2. A compound according to claim 1, wherein M is selected from cobalt (III), rhodium (III) iridium (III), iron (II), ruthenium (II), or osmium (II).

3. A compound according to claim 2, wherein M is cobalt (III).

4. A compound according to claim 1 wherein each of $R^1$, $R^2$, $R^3$, $R^8$, $R^9$, and $R^{10}$ is independently selected from H, $OR^{24}$, $OCOR^{24}$, $OC(O)OR^{24}$, $OP(O)(OR^{24})(OR^{25})$, $OP(O)R^{24}R^{25}$, $SR^{24}$, $SCOR^{24}$, $SC(O)OR^{24}$, $SP(O)(OR^{24})(OR^{25})$, $SP(O)R^{24}R^{25}$, $NR^{24}R^{25}$, $NR^{24}COR^{25}$, $NR^{24}CO_2R^{25}$ or $NR^{26}P(O)(OR^{24})(OR^{25})$, or —Y—$R^{27}$;
wherein each of $R^{24}$, $R^{25}$ and $R^{26}$ are independently selected from H and $C_1$-$C_{10}$ alkyl, polyethylene glycol (PEG) and polyether groups;
wherein Y is a chemical bond or a linker moiety;
wherein Z is selected from a chemical bond, acetylene, disubstituted phenylene, naphthalene, anthracene, pyrene or similar chemically rigid spacer, and
wherein $R^{27}$ is a targeting moiety.

5. A compound according to claim 4, wherein the targeting moiety is a small molecule, peptide, protein or antibody.

6. A compound according to claim 5, wherein the targeting moiety has a high affinity for a target site such that when administered, the compound binds to the target site via the targeting moiety.

7. A compound according to claim 1,
wherein $R^1$, $R^3$, $R^6$, $R^7$, $R^8$, $R^{10}$, $R^{13}$ and $R^{14}$ are independently selected from H, $OR^{36}$, $OCOR^{36}$, $OC(O)OR^{36}$, $OP(O)(OR^{36})(OR^{37})$, $OP(O)R^{36}R^{37}$, $SR^{36}$, $SCOR^{36}$, $SC(O)OR^{36}$, $SP(O)(OR^{36})(OR^{37})$, $SP(O)R^{36}R^{37}$, $NR^{36}R^{37}$, $NR^{37}COR^{36}$, $NR^{37}CO_2R^{36}$ or $NR^{38}P(O)(OR^{36})(OR^{37})$; and wherein $R^{36}$, $R^{37}$ and $R^{38}$ are independently selected from H, $C_1$-$C_{10}$ alkyl, polyethylene glycol (PEG) and polyether groups.

8. A compound according to claim 7, wherein $R^3$ and $R^{10}$ are $NH_2$ and $R^1$ and $R^8$ are H.

9. A compound according to claim 1, wherein the compound is configured to capture and retain an anionic target species.

10. A compound according to claim 9, wherein the anionic target species is a radiolabel anion.

11. A compound according to formula VI;

$$[T \subset M_4L_6] \cdot X_n \qquad (VI)$$

wherein T is a target species retained within the cavity of the compound according to formula I; and wherein L, M, X and n are as defined in claim 1.

12. The compound of claim 11, wherein T is an anionic target species comprising a radioactive isotope selected from the group carbon-11 ($^{11}C$), fluorine-18 ($^{18}F$), copper-64 ($^{64}Cu$), gallium-68 ($^{68}Ga$), zirconium-89 ($^{89}Zr$), gallium-67 ($^{67}Ga$), technetium-99m ($^{99m}Tc$), indium-111 ($^{111}In$), copper-67 ($^{67}Cu$), rhenium-186 ($^{186}Re$), rhenium-188 ($^{188}Re$), lutetium-177 ($^{177}Lu$), astatine-211 ($^{211}At$), and actinium-225 ($^{225}Ac$).

13. A pharmaceutical composition comprising the compound of claim 1 and a pharmaceutically acceptable excipient, carrier, vehicle or diluent.

14. A compound according to claim 1 for use as a diagnostic marker or label.

15. A compound according to claim 1 for use in vivo.

16. A method of preparing a compound according to formula I in claim 1, the method comprising the steps:
  a. providing a first solution comprising transition metal ions M having 7 d-shell valence electrons, and a second solution comprising ligands according to formula II;
  b. mixing the first solution with the second solution;
  c. oxidising the transition metal ions M in the resulting compound, such that the structure of the complex becomes fixed.

17. A method of preparing a compound according to formula VI in claim 11, $$[M_4L_6] \cdot X_n \cdot T \qquad (VI)$$

the method comprising the steps:
  a. providing a compound according to formula I;
  b. providing a target species T;
  c. combining the compound according to formula I with the target species to form the compound according to formula VI.

18. The method of claim 17, wherein the compound according to formula I is provided in a solution.

19. The method of claim 17, wherein the target species is provided in a solution.

20. A method of using the compound according to formula VI in claim 11 for diagnosis comprising the steps;
  providing a compound according to formula VI;
  administering the compound to a subject; and
  monitoring the location and/or movement of the compound within the subject.

* * * * *